United States Patent
Ralph et al.

(10) Patent No.: US 6,723,127 B2
(45) Date of Patent: Apr. 20, 2004

(54) ARTIFICIAL INTERVERTEBRAL DISC HAVING A WAVE WASHER FORCE RESTORING ELEMENT

(75) Inventors: James D. Ralph, Seaside Park, NJ (US); Stephen Tatar, Montville, NJ (US); Joseph P. Errico, Kirkland, WA (US)

(73) Assignee: Spine Core, Inc., Summit, NJ (US)

( * ) Notice: Subject to any disclaimer, the term of this patent is extended or adjusted under 35 U.S.C. 154(b) by 0 days.

(21) Appl. No.: 10/177,377

(22) Filed: Jun. 21, 2002

(65) Prior Publication Data

US 2003/0014112 A1 Jan. 16, 2003

Related U.S. Application Data

(63) Continuation-in-part of application No. 09/906,117, filed on Jul. 16, 2001, now Pat. No. 6,468,310, and a continuation-in-part of application No. 09/906,118, filed on Jul. 16, 2001, now Pat. No. 6,527,806.

(51) Int. Cl.⁷ .................................................. A61F 2/44
(52) U.S. Cl. ............................... 623/17.13; 623/17.15; 623/17.16
(58) Field of Search .......................... 623/17.11, 17.13, 623/17.14, 17.15, 17.16; 606/61

(56) References Cited

U.S. PATENT DOCUMENTS

| | | | |
|---|---|---|---|
| 5,458,642 A | 10/1995 | Beer et al. | |
| 5,556,431 A | 9/1996 | Buttner-Janz | |
| 5,562,738 A | 10/1996 | Boyd et al. | |
| 5,674,296 A | 10/1997 | Bryan et al. | |
| 5,676,701 A | 10/1997 | Yuan et al. | |
| 5,676,702 A | 10/1997 | Ratron | |
| 5,683,465 A | 11/1997 | Shinn et al. | |
| 5,755,796 A | 5/1998 | Ibo et al. | |
| 5,827,328 A | 10/1998 | Butterman | |
| 5,865,846 A | 2/1999 | Bryan et al. | |
| 5,888,226 A | 3/1999 | Rogozinski | |
| 5,895,428 A | 4/1999 | Berry | |
| 5,899,941 A | 5/1999 | Nishijima | |
| 5,928,284 A | * 7/1999 | Mehdizadeh | 623/17.13 |
| 5,989,291 A | 11/1999 | Ralph et al. | |
| 6,001,130 A | 12/1999 | Bryan et al. | |
| 6,019,792 A | 2/2000 | Cauthen | |
| 6,039,763 A | 3/2000 | Shelokov | |
| 6,063,121 A | 5/2000 | Xavier et al. | |
| 6,113,637 A | 9/2000 | Gill et al. | |
| 6,136,031 A | 10/2000 | Middleton | |
| 6,146,421 A | 11/2000 | Gordon et al. | |
| 6,156,067 A | 12/2000 | Bryan et al. | |
| 6,179,874 B1 | 1/2001 | Cauthen | |
| 6,228,118 B1 | 5/2001 | Gordon | |
| 6,231,609 B1 | * 5/2001 | Mehdizadeh | 623/17.11 |
| 6,454,806 B1 | * 9/2002 | Cohen et al. | 623/17.15 |
| 6,520,996 B1 | * 2/2003 | Manasas et al. | 623/23.5 |
| 6,527,804 B1 | * 3/2003 | Gauchet et al. | 623/17.12 |
| 6,579,320 B1 | * 6/2003 | Gauchet et al. | 623/17.15 |
| 2002/0128714 A1 | * 9/2002 | Manasas et al. | 623/17.15 |
| 2003/0040801 A1 | * 2/2003 | Ralph et al. | 623/17.13 |

\* cited by examiner

*Primary Examiner*—Eduardo C. Robert
(74) *Attorney, Agent, or Firm*—Joseph P. Errico, Esq.; Timothy J. Brotree, Esq.

(57) ABSTRACT

An artificial disc having a pair of opposing plates for seating against opposing vertebral bone surfaces, separated by a wave washer having a circumferential extent surrounding a central bore. Various wave washer embodiments disclosed include circumferential extents that are ring-shaped, spiral-shaped, straight, bowed, grooved, wavy, thinning, thickening, and slotted. Various central bores disclosed include simple bores and bores that form a curvate socket. Various plate embodiments disclosed include plates having, on inwardly facing surfaces, a flat surface, a circular recess, or a ball-shaped protuberance that is mateable with the curvate socket. The wave washers are disposable between the plates, through various disclosed couplings, so that the plates compress, rotate and angulate freely relative to one another, enabling the artificial disc to mimic a healthy natural intervertebral disc.

20 Claims, 8 Drawing Sheets

FIG. 1.1
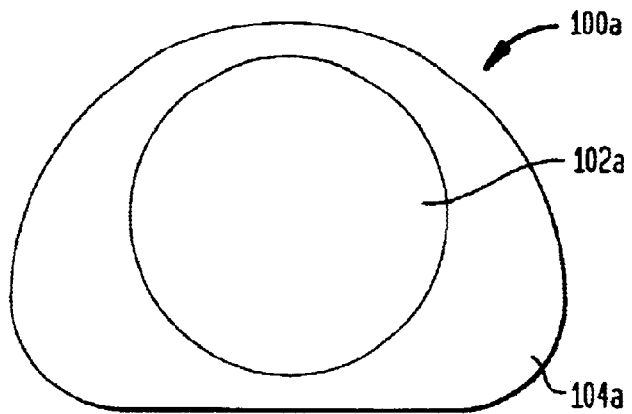
FIG. 1.2
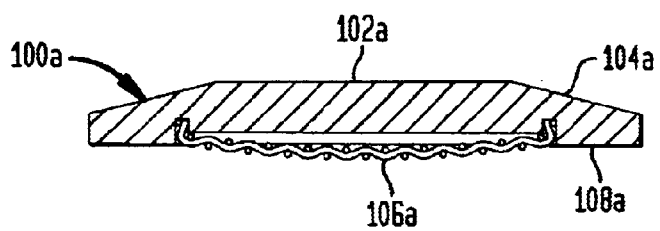
FIG. 1.3
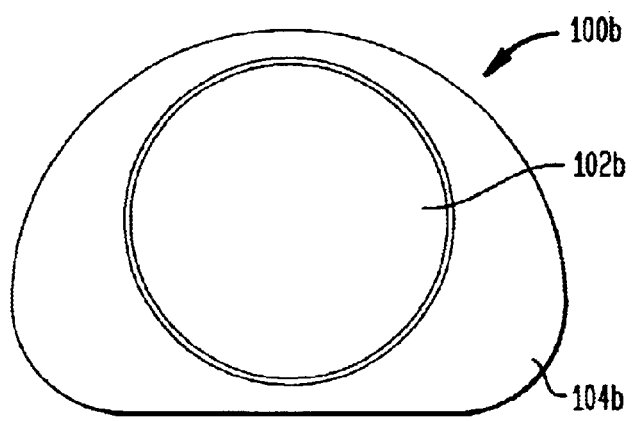
FIG. 1.4
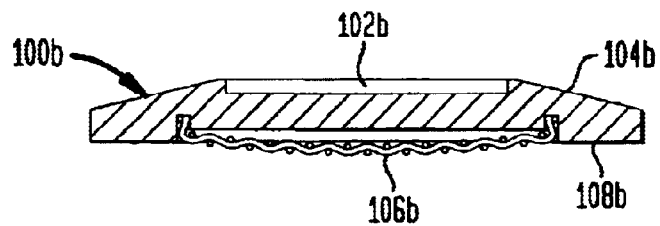

FIG. 1.5
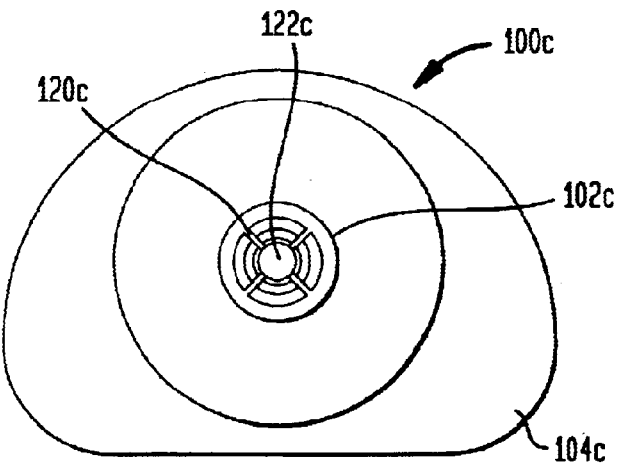
FIG. 1.6
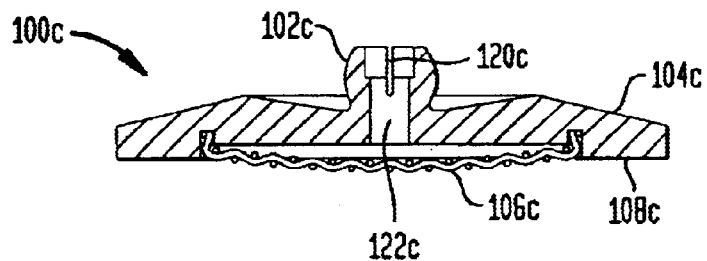
FIG. 1.7
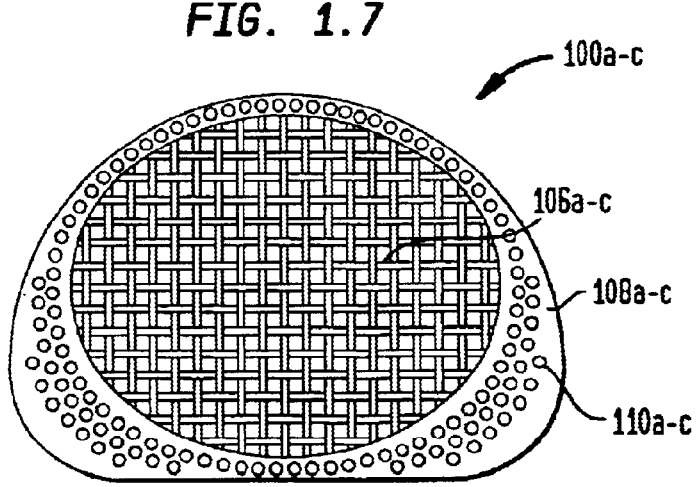

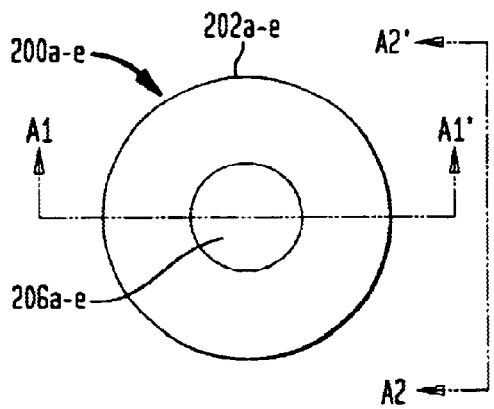
FIG. 2.1
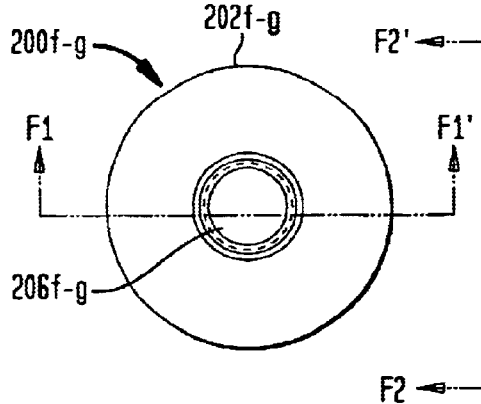
FIG. 2.4
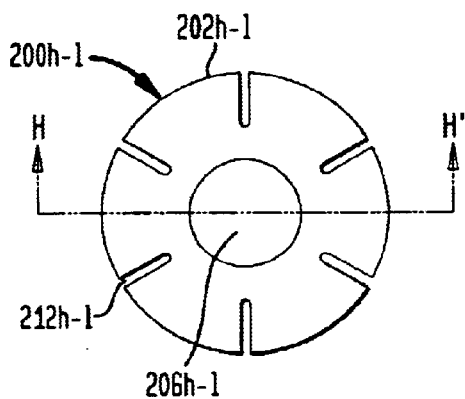
FIG. 2.2
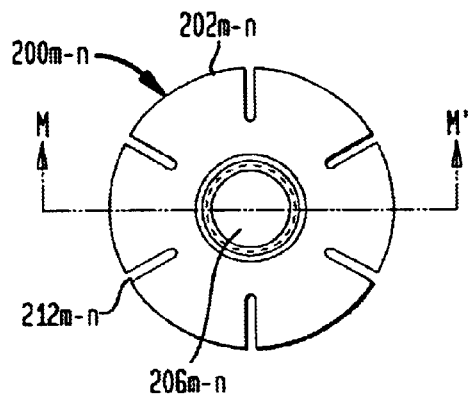
FIG. 2.5
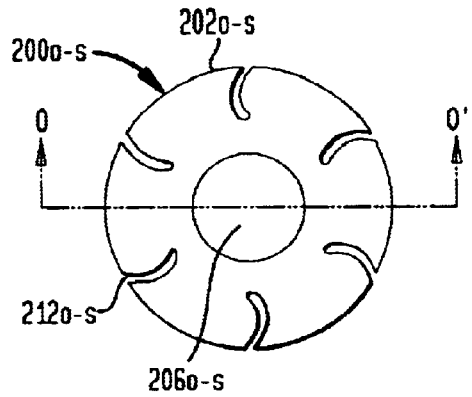
FIG. 2.3
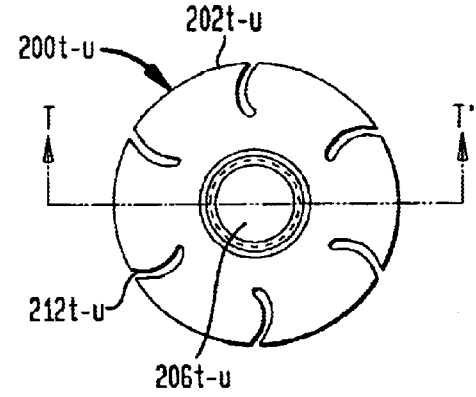
FIG. 2.6

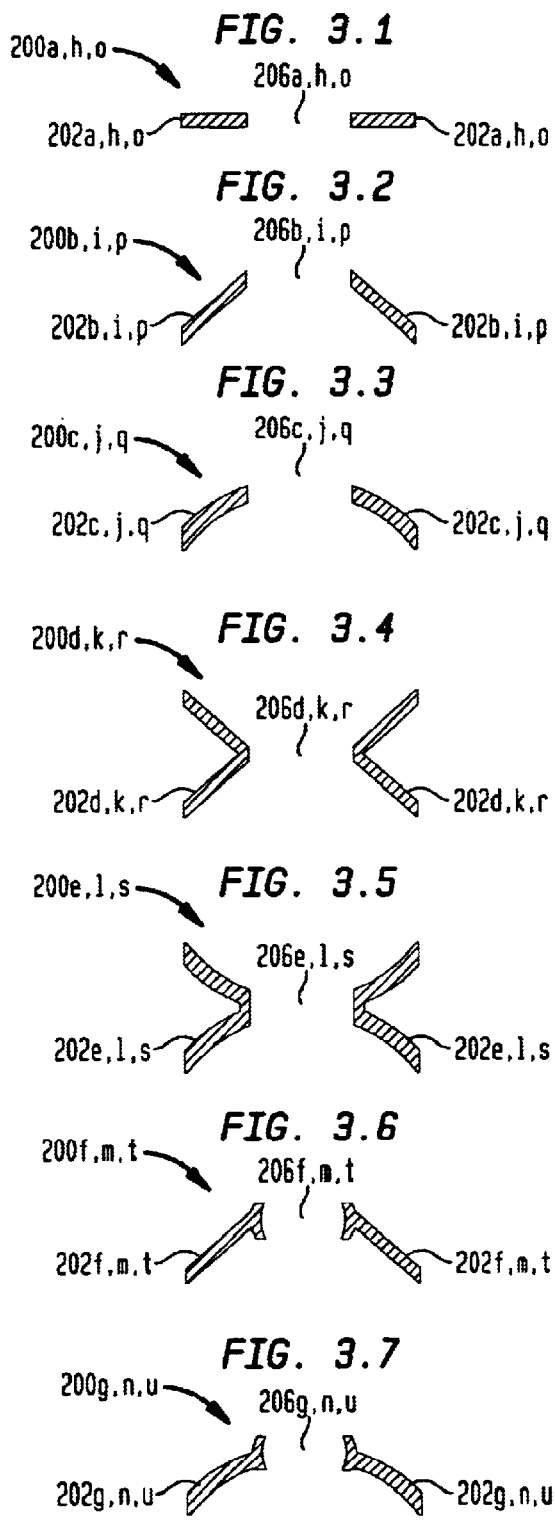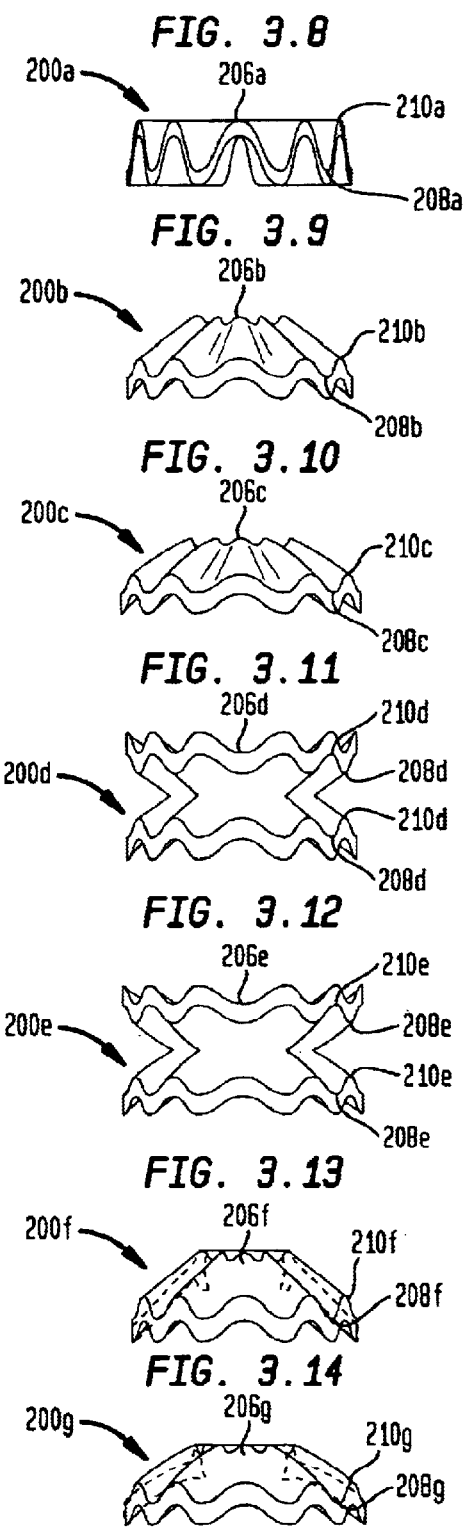

FIG. 4.1 
FIG. 4.2 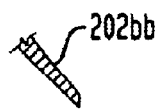
FIG. 4.3 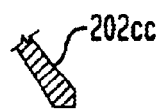
FIG. 4.4 
FIG. 4.5 
FIG. 4.6 
FIG. 4.7 
FIG. 4.8 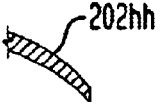
FIG. 4.9 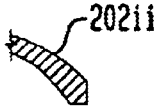
FIG. 4.10 
FIG. 4.11 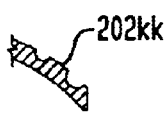
FIG. 4.12 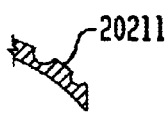
FIG. 4.13 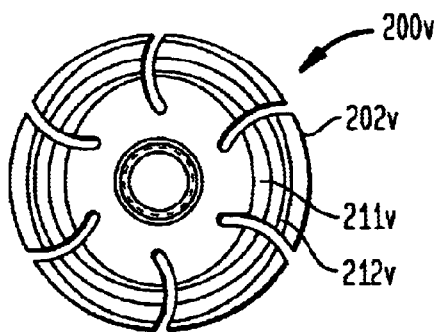
FIG. 4.14 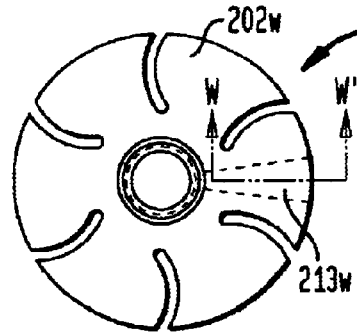
FIG. 4.15 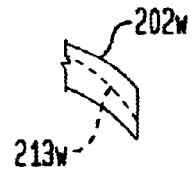

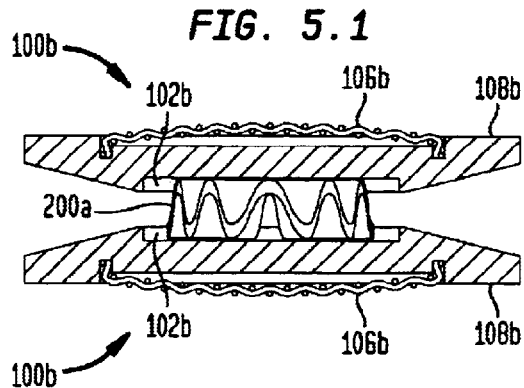
FIG. 5.1
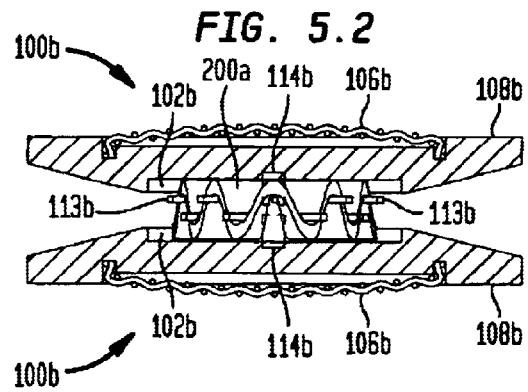
FIG. 5.2
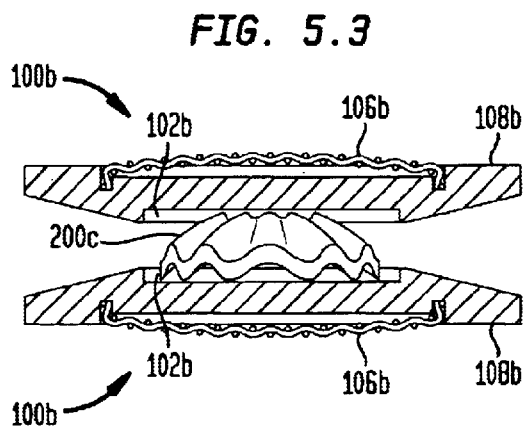
FIG. 5.3
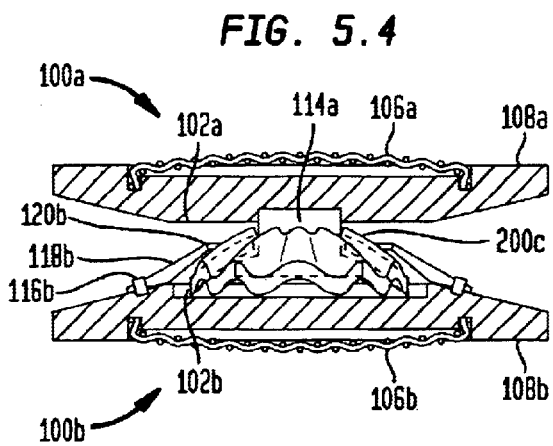
FIG. 5.4
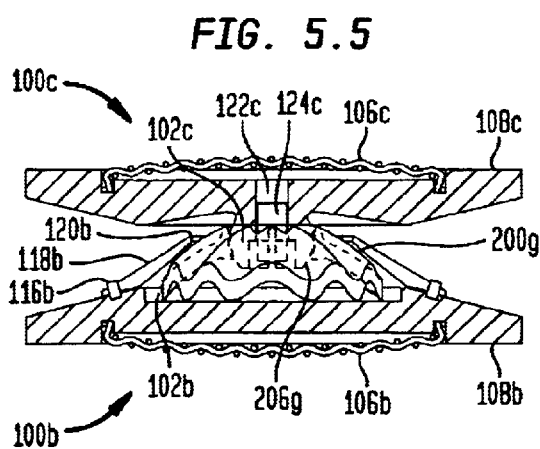
FIG. 5.5
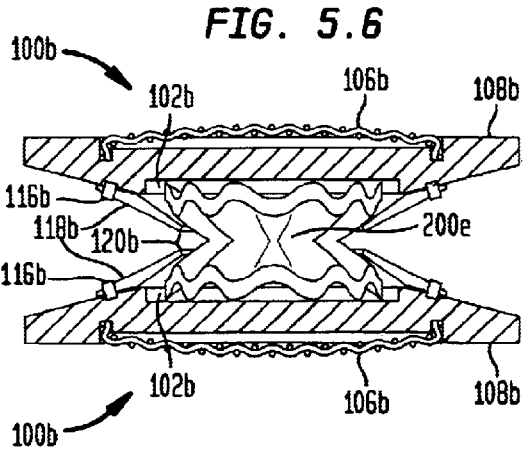
FIG. 5.6

FIG. 6.1
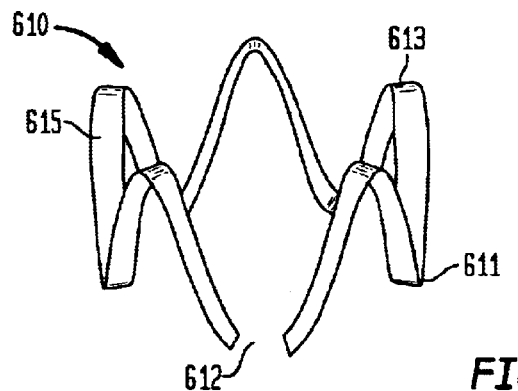
FIG. 6.2
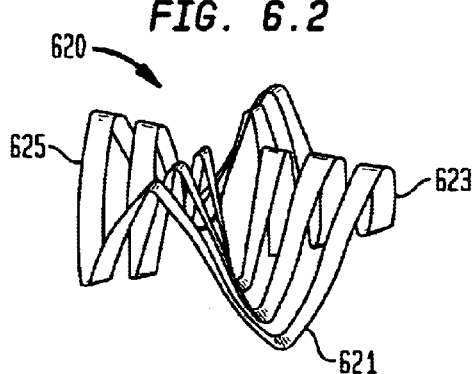
FIG. 6.3
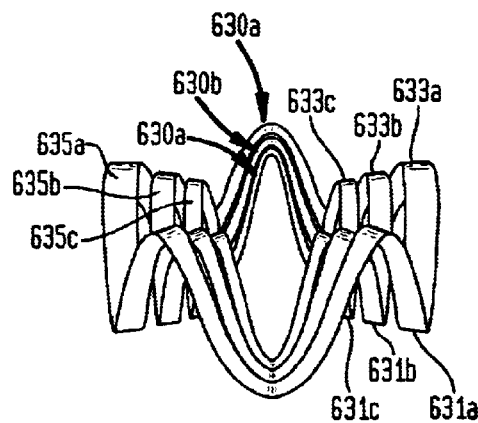
FIG. 6.4
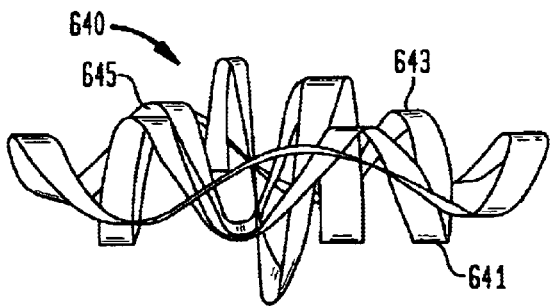
FIG. 6.5
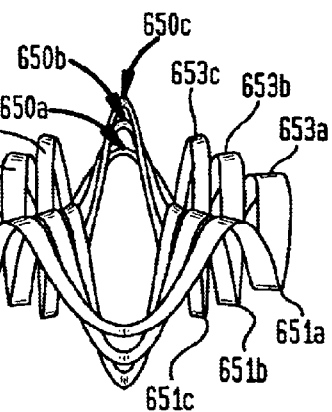

ARTIFICIAL INTERVERTEBRAL DISC HAVING A WAVE WASHER FORCE RESTORING ELEMENT

CROSS REFERENCE TO RELATED APPLICATIONS

This application is a continuation-in-part of U.S. patent application Ser. No. 09/906,117 entitled "Intervertebral Spacer Device Having a Wave Washer Force Restoring Element", filed Jul. 16, 2001, now U.S. Pat. No. 6,468,310, and a continuation-in-part of U.S. patent application Ser. No. 09/906,118 entitled "Intervertebral Spacer Device Having a Spiral Wave Washer Force Restoring Element", filed Jul. 16, 2001, now U.S. Pat. No. 6,527,806.

FIELD OF THE INVENTION

This invention relates generally to a spinal implant assembly for implantation into the intervertebral space between adjacent vertebral bones to simultaneously provide stabilization and continued flexibility and proper anatomical motion, and more specifically to such a device that utilizes a wave washer force restoring element.

BACKGROUND OF THE INVENTION

The bones and connective tissue of an adult human spinal column consists of more than 20 discrete bones coupled sequentially to one another by a tri-joint complex that consists of an anterior disc and the two posterior facet joints, the anterior discs of adjacent bones being cushioned by cartilage spacers referred to as intervertebral discs. These more than 20 bones are anatomically categorized as being members of one of four classifications: cervical, thoracic, lumbar, or sacral. The cervical portion of the spine, which comprises the top of the spine, up to the base of the skull, includes the first 7 vertebrae. The intermediate 12 bones are the thoracic vertebrae, and connect to the lower spine comprising the 5 lumbar vertebrae. The base of the spine is the sacral bones (including the coccyx). The component bones of the cervical spine are generally smaller than those of the thoracic spine, which are in turn smaller than those of the lumbar region. The sacral region connects laterally to the pelvis. While the sacral region is an integral part of the spine, for the purposes of fusion surgeries and for this disclosure, the word spine shall refer only to the cervical, thoracic, and lumbar regions.

The spinal column is highly complex in that it includes these more than 20 bones coupled to one another, housing and protecting critical elements of the nervous system having innumerable peripheral nerves and circulatory bodies in close proximity. In spite of these complications, the spine is a highly flexible structure, capable of a high degree of curvature and twist in nearly every direction.

Genetic or developmental irregularities, trauma, chronic stress, tumors, and degenerative wear are a few of the causes that can result in spinal pathologies for which surgical intervention may be necessary. A variety of systems have been disclosed in the art that achieve immobilization and/or fusion of adjacent bones by implanting artificial assemblies in or on the spinal column. The region of the back that needs to be immobilized, as well as the individual variations in anatomy, determine the appropriate surgical protocol and implantation assembly. With respect to the failure of the intervertebral disc, the interbody fusion cage has generated substantial interest because it can be implanted laparoscopically into the anterior of the spine, thus reducing operating room time, patient recovery time, and scarification.

Referring now to FIGS. 7 and 8, in which a side perspective view of an intervertebral body cage and an anterior perspective view of a post implantation spinal column are shown, respectively, a more complete description of these devices of the prior art is herein provided. These cages 10 generally comprise tubular metal body 12 having an external surface threading 14. They are inserted transverse to the axis of the spine 16, into preformed cylindrical holes at the junction of adjacent vertebral bodies (in FIG. 8 the pair of cages 10 are inserted between the fifth lumbar vertebra (L5) and the top of the sacrum (S1)). Two cages 10 are generally inserted side by side with the external threading 14 tapping into the lower surface of the vertebral bone above (L5), and the upper surface of the vertebral bone (S1) below. The cages 10 include holes 18 through which the adjacent bones are to grow. Additional materials, for example autogenous bone graft materials, may be inserted into the hollow interior 20 of the cage 10 to incite or accelerate the growth of the bone into the cage. End caps (not shown) are often utilized to hold the bone graft material within the cage 10.

These cages of the prior art have enjoyed medical success in promoting fusion and grossly approximating proper disc height. It is, however, important to note that the fusion of the adjacent bones is an incomplete solution to the underlying pathology as it does not cure the ailment, but rather simply masks the pathology under a stabilizing bridge of bone. This bone fusion limits the overall flexibility of the spinal column and artificially constrains the normal motion of the patient. This constraint can cause collateral injury to the patient's spine as additional stresses of motion, normally borne by the now-fused joint, are transferred onto the nearby facet joints and intervertebral discs. It would therefore, be a considerable advance in the art to provide an implant assembly which does not promote fusion, but, rather, which nearly completely mimics the biomechanical action of the natural disc cartilage, thereby permitting continued normal motion and stress distribution.

It is, therefore, an object of the invention to provide an intervertebral spacer that stabilizes the spine without promoting a bone fusion across the intervertebral space.

It is further an object of the invention to provide an implant device that stabilizes the spine while still permitting normal motion.

It is further an object of the invention to provide a device for implantation into the intervertebral space that does not promote the abnormal distribution of biomechanical stresses on the patient's spine.

It is further an object of the invention to provide an artificial disc that has an plate attachment device (for attaching the plates of the artificial disc to the vertebral bones between which the disc is implanted) with superior gripping and holding strength upon initial implantation and thereafter.

It is further an object of the invention to provide an artificial disc plate attachment device that deflects during insertion of the artificial disc between vertebral bodies.

It is further an object of the invention to provide an artificial disc plate attachment device that conforms to the concave surface of a vertebral body.

It is further an object of the invention to provide an artificial disc plate attachment device that does not restrict the angle at which the artificial disc can be implanted.

It is further an object of the invention to provide an artificial disc that supports tension loads.

It is further an object of the invention to provide an artificial disc that provides a centroid of motion centrally located within the intervertebral space.

Other objects of the invention not explicitly stated will be set forth and will be more clearly understood in conjunction with the descriptions of the preferred embodiments disclosed hereafter.

SUMMARY OF THE INVENTION

The preceding objects are achieved by the invention, which is an artificial intervertebral disc or intervertebral spacer device comprising a pair of support members (e.g., spaced apart plates), each with an exterior surface. Because the artificial disc is to be positioned between the facing surfaces of adjacent vertebral bodies, the plates are arranged in a substantially parallel planar alignment (or slightly offset relative to one another in accordance with proper lordotic angulation) with the exterior surfaces facing away from one another. The plates are to mate with the vertebral bodies so as to not rotate relative thereto, but rather to permit the spinal segments to axially compress and bend relative to one another in manners that mimic the natural motion of the spinal segment. This natural motion is permitted by the performance of a spring disposed between the secured plates, and the securing of the plates to the vertebral bone is achieved through the use of a vertebral body contact element including, for example, a convex mesh attached to the exterior surface of each plate. Each convex mesh is secured at its perimeter, by laser welds, to the exterior surface of the respective plate. While domed in its initial undeflected conformation, the mesh deflects as necessary during insertion of the artificial disc between vertebral bodies, and, once the artificial disc is seated between the vertebral bodies, the mesh deforms as necessary under anatomical loads to reshape itself to the concave surface of the vertebral endplate. Thus, the wire mesh is deformably reshapeable under anatomical loads such that it conformably deflects against the concave surface to securably engage the vertebral body endplate. Stated alternatively, because the wire mesh is convexly shaped and is secured at its perimeter to the plate, the wire mesh is biased away from the plate but moveable toward the plate (under a load overcoming the bias; such a load is present, for example, as an anatomical load in the intervertebral space) so that it will securably engage the vertebral body endplate when disposed in the intervertebral space. This affords the plate having the mesh substantially superior gripping and holding strength upon initial implantation, as compared with other artificial disc products. The convex mesh further provides an osteoconductive surface through which the bone may ultimately grow. The mesh preferably is comprised of titanium, but can also be formed from other metals and/or non-metals. Inasmuch as the mesh is domed, it does not restrict the angle at which the artificial disc can be implanted. It should be understood that while the flexible dome is described herein preferably as a wire mesh, other meshed or solid flexible elements can also be used, including flexible elements comprises of non-metals and/or other metals. Further, the flexibility, deflectability and/or deformability need not be provided by a flexible material, but can additionally or alternatively be provided mechanically or by other means.

To enhance the securing of the plates to the vertebral bones, each plate further comprises at least a lateral porous ring (which may be, for example, a sprayed deposition layer, or an adhesive applied beaded metal layer, or another suitable porous coating known in the art). This porous ring permits the long-term ingrowth of vertebral bone into the plate, thus permanently securing the prosthesis within the intervertebral space. The porous layer may extend beneath the domed mesh as well, but is more importantly applied to the lateral rim of the exterior surface of the plate that seats directly against the vertebral body.

The spring disposed between the plates provides a strong restoring force when a compressive load is applied to the plates, and also permits rotation and angulation of the two plates relative to one another. While a wide variety of embodiments are contemplated, a preferred spring includes a wave washer utilized as the restoring force providing element. In general, a wave washer is one of the strongest configurations for a spring, and is highly suitable for use as a force restoring providing subassembly for use in an intervertebral spacer element that must endure considerable cyclical loading in an active human adult. A compressive load applied to the plates causes a corresponding compression of the wave washer, which is turn causes a restoring force to be applied to the plates. The wave washer deflects appropriately under the load, only to spring back to its undeflected shape upon the unloading.

In particular, in order for the overall device to mimic the mechanical flexibility of the natural disc, it is desirable that the spring provide restoring forces that (1) are directed outward against the opposing plates, when a compressive load is applied to the plates; (2) that permit lateral bending and flexion and extension bending of the plates relative to parallel; (3) that do not permit lateral translation of the plates relative to one another during such bending; and (4) that do not substantially interfere with the rotation of the opposing plates relative to one another. The wave washers disclosed herein provide such functionality.

The wave washers of the invention have a circumferential extent surrounding a central bore. The circumferential extent is concentrically wavy, such that the extent undulates along a concentric path around the central bore to form radially extending valleys and peaks, while preferably maintaining a constant radius. Stated equivalently with regard to the most basic wave washer embodiments of the invention, which resemble traditional wave washers, the wave washer is a simple round washer having a circumferential extent that comprises a flat round ring, except that while maintaining a constant curvature of radius in the plane normally defined by the washer, the circumferential extent rises and falls in a wave-like curve. Whereas a standard (non-wave) washer has a circumferential extent that is confined to the x-y plane, the wave washer has a circumferential extent that extends in the x-y plane but undulates in the z-axis. Herein, the top and bottom of a wave washer shall be defined as the planes defined by the lowest and highest points of the undulations, respectively. In some embodiments, the circumferential extent is continuous (i.e., has no slots). In other embodiments, the circumferential extent has at least one radially extending slot. In still other embodiments, the circumferential extent has at least one radially extending and spiraling slot. The thickness of the circumferential extent; the frequency, amplitude, and configuration of the waves; and/or the number and configuration of the slots can be varied to accommodate any desired application, inasmuch as varying the dimensions will affect the behavior of the wave washer in expansion and retraction.

The restoring force of a wave washer is proportional to the elastic properties of the material. As a compressive load is applied to the wave washer, the forces are directed down onto the peaks and up against the valleys. A significant fraction of these forces are immediately translated into hoop stresses that apply stresses directly toward radially expanding the wave washer. This hoop stress is also counterbalanced by the material strength of the wave washer. The strain of the material causes a deflection in the height of the washer and a slight radial expansion. The slots in the slotted embodiments permit the compressive load that is applied to the wave washer down onto the peaks and up against the valleys to cause the wave washer to deflect such that the slots close. Thus, a difference between a slotted washer and a continuous washer is that the continuous washer responds to a compressive load by primarily deflecting radially (with a very high stress to deflection ratio), whereas the slotted washer primarily deflects circumferentially, closing the slots (which is characteristic of a much lower stress to deflection ratio). Stated equivalently, a wave washer responds to a compressive load by deflecting compressively, and either radially or circumferentially. With at least one slot formed in the washer, it expands and retracts far more elastically than a continuous washer. It should be understood that wave washers other than those shown are contemplated by the invention, including but not limited to wave washers having a circumferential extent that does not have a uniformly wide radius.

As described above, the most basic wave washer of the invention has a circumferential extent that defines a circumference of 360 degrees (or less if the wave washer includes a radial slot that passes completely through the circumferential extent). Another wave washer embodiment of the invention, instead of being ring-shaped, is spiral-shaped, having a circumferential extent that defines a circumference of more than 360 degrees, and preferably more than 720 degrees, or more depending on the specific anatomical needs of the patient. The undulations of the wave washer in the z-axis may be such that the arches are aligned, or misaligned. In yet another wave washer embodiment of the invention, instead of using a spiral-shaped wave washer, multiple concentric ring-shaped wave washers can be used in conjunction with one another to achieve a similar functional result.

Still another wave washer embodiment of the invention is also spiral-shaped, but has an amplitude of the undulations that decreases in the radial direction. The wave washer thereby takes on the edge-on appearance of a spiral galaxy, having a thicker central portion, and a flatter edge. In this case, the restoring force varies according to the number of spirals of the washer and according to the number of spirals that are engaged (more radially distal spirals are engaged as the deflection of the washer increases). More specifically, as a compressive load is applied by a pair of plates against the top and bottom of a spiral wave washer, the forces are first directed against the peaks of the undulating waves at the center of the spiral, and are then increasingly directed against the peaks of the outer portions of the spiral. In a further wave washer embodiment of the invention, instead of using a spiral-shaped wave washer with radially decreasing undulation amplitudes, multiple concentric ring-shaped wave washers can be used in conjunction with one another, positioned so that those with smaller undulation amplitudes are more radially distant from the center of the grouped washers, to achieve a similar functional result. It should be understood that in either of these types of embodiments, the wave washers can be formed such that the undulation amplitudes increase, rather than decrease, with their radial distance from the center of the washer, or such that the undulation amplitudes vary in size either randomly or according to other patterns.

With regard to additional wave washer embodiments, changing the configuration of the circumferential extent in other ways modifies the magnitude of the compressive load support and restoring force provided by the wave washer. For clarity and conciseness, the other circumferential extent configurations discussed herein are illustrated with regard to wave washers having circumferential extents that are ring-shaped (as opposed to spiral-shaped) and thicker compared to the wave washer embodiments summarized above (as those summarized embodiments are illustrated), however it should be understood that the additional circumferential extent variations discussed herein can be applied individually or in various combinations to the spiral-shaped, concentric, and/or radially varying undulation amplitude configurations, without departing from the scope of the invention.

For example, a variety of circumferential extents are illustrated and discussed herein. In some embodiments, the circumferential extent is generally planar (e.g., the extent extends in a plane and all of the waves undulate perpendicular to that plane). In other embodiments, the circumferential extent is generally conical (e.g., the extent extends to define a conical surface concentric with the central bore and the waves undulate perpendicular to that surface at their respective positions on the surface) and radially straight, such that the height of the wave washer is linearly related to the radial width of the circumferential extent. In still other embodiments, the circumferential extent is generally semispherical (e.g., the extent extends to define a semispherical surface concentric with the central bore and the waves undulate perpendicular to that surface at their respective positions on the surface) and radially bowed, such that the height of the wave washer is not linearly related to the radial width of the circumferential extent (but rather the wave washer may, for example, be parabolic in shape). In still other embodiments, the circumferential extent extends radially downwardly from the central bore. In still other embodiments, the circumferential extent is doubled, with a lower portion extending radially downwardly from the central bore and an upper portion extending radially upwardly from the central bore. By changing the circumferential extent from a generally planar configuration to a generally conical or generally semispherical configuration, the resting height of the washer is increased and the radial expansion potential of the washer is increased while the structural integrity of the washer is enhanced. The shape and direction of the circumferential extent can be varied to accommodate desired applications, inasmuch as varying the dimensions will affect the behavior of the wave washer in expansion and retraction.

Also, for example, additional configurations of the circumferential extent are possible, and are illustrated and discussed herein, to affect the behavior of the wave washer in expansion and retraction. In some embodiments, in addition to the concentric waviness common to all of the wave washer embodiments, the circumferential extent has at least one concentric or radial characteristic that alters the performance of the wave washer in expansion and/or retraction. More specifically, in some embodiments, the circumferential extent is not only concentrically wavy, but is also radially wavy. In other embodiments, the circumferential extent is radially thinning (the portion of the extent near the central bore is thicker than the portion of the extent near the outer edge of the washer). In still other embodiments, the circumferential extent is radially thickening (the portion of the extent near the central bore is thinner than the portion of the extent near the outer edge of the washer). In still other embodiments, the circumferential extent is concentrically grooved, having grooves that are similarly dimensioned to one another regardless of their relative radial distance from the central bore, or grooves that vary in dimension from one another depending on their relative radial distance from the central bore. These alterations, depending on the configuration, cause certain portions (e.g., grooved, thinner, or more wavy portions) of the circumferential extent to expand more readily than other portions (e.g., non-grooved, thicker or less wavy portions).

It should be noted that with regard to the waves of the wave washers of the invention, one or both of the depth and the width of each wave can be (1) decreasing along the length of the wave from the outer edge of the washer toward the central bore, (2) increasing along the length of the wave from the outer edge of the washer toward the central bore, (3) uniform along the length of the wave from the outer edge of the washer toward the central bore, or (4) varied along the length of each wave from the outer edge of the washer toward the central bore, either randomly or according to a pattern. Moreover, it can be the case that each wave is not formed similarly to one or more other waves, but rather one or more waves are formed in any of the above-mentioned fashions, while one or more other waves are formed in another of the above-mentioned fashions or other fashions. It should be clear that any wave pattern can be implemented without departing from the scope of the invention. By making the wave pattern non-uniform, certain portions of the circumferential extent give more readily than other portions, and therefore the behavior of the wave washer in expansion and retraction can be modified and/or controlled.

For disposing the wave washer (whichever wave washer embodiment is chosen for the clinical application) between the plates, each wave washer embodiment has at least one feature suitable for this purpose, and the plates of the artificial disc comprise cooperating features suitable for this purpose. With regard to the wave washer features, each wave washer embodiment has a central bore and at least one end that expands and retracts as described above. The central bore of some wave washer embodiments forms a curvate socket on a narrow end of the wave washer, for coupling with a ball-shaped protuberance on a plate as described below.

With regard to the structure and coupling features of the plates, three plate embodiments are illustrated and described herein, although other suitable plate embodiments can be used with the invention. Each of the three plate embodiments has the above described convex mesh on its outwardly facing surface, although other vertebral body attachment devices and mechanisms can be used without departing from the scope of the invention. Each of the three plate embodiments has a different inwardly facing surface from the other two plate embodiments. The first plate embodiment has a flat inwardly facing surface that accepts a fastener (e.g., a screw, plug, dowel or rivet; a rivet is used herein as an example) for rotatably securing thereto a narrow end of a wave washer having a circumferential extent that is generally conical or generally semispherical, and/or that accepts a flanged (and preferably rotatable) fastener (e.g., a screw, plug, dowel, rivet, or spoked post; a rotatable spoked post is used herein as an example) for securing thereto a wave washer having a circumferential extent that is generally planar. The second plate embodiment has a circular recess on its inwardly facing surface, for rotationally housing an end of a wave washer and allowing the end to expand in unrestricted fashion when the wave washer is compressed. The third plate embodiment has a semispherical (e.g., ball-shaped) protuberance on its inwardly facing surface, for rotatably and angulatably holding a narrow end of a wave washer, which narrow end includes a curvate socket as described below.

The semispherical protuberance has an axial bore that receives a deflection preventing element (e.g., a rivet, plug, dowel, or screw; a rivet is used herein as an example). Prior to the insertion of the rivet, the ball-shaped protuberance can deflect radially inward (so that the ball-shaped protuberance contracts). The insertion of the rivet eliminates the capacity for this deflection. The curvate socket, having a substantially constant radius of curvature that is also substantially equivalent to the radius of the ball-shaped protuberance, accommodates the ball-shaped protuberance for free rotation and angulation once the ball-shaped protuberance is disposed in the curvate socket, but in the ball-shaped protuberance's undeflected state, the ball-shaped protuberance cannot fit through the opening leading to the curvate socket. Therefore, the deflectability of the ball-shaped protuberance, prior to the insertion of the rivet, permits the ball-shaped protuberance to be inserted into the curvate socket. Subsequent introduction of the rivet into the axial bore of the ball-shaped protuberance prevents the ball-shaped protuberance from deflecting, and thus prevents the ball-shaped protuberance from escaping the socket. Thereby, the ball-shaped protuberance can be secured in the curvate socket so that it rotates and angulates therein through a range of angles, thus permitting the plates to rotate and angulate relative to one another through a corresponding range of angles equivalent to the fraction of normal human spine rotation and angulation (to mimic normal disc rotation and angulation).

With the three plate embodiments, the various wave washer embodiments, and the several manners in which they may be coupled together, it is possible to assemble a variety of artificial disc embodiments. Many examples are described herein, although many permutations that are contemplated and encompassed by the invention are not specifically identified herein, but are readily identifiable with an understanding of the invention as described. For example, any of the wave washers can be disposed between circular recesses of opposing plates. Also for example, all wave washers having a curvate socket can have the curvate socket coupled with a ball-shaped protuberance on a plate. Also for example, all wave washers having a simple bore (i.e., without a curvate socket) can have the simple bore coupled with a flat inwardly facing surface of a plate using a fastener (e.g., a rotatable spoked post or a screw or a rivet). Also for example, each wave washer having a wide end (e.g., wave washers having a circumferential extent that is generally conical or generally semispherical) can be disposed with its wide end in a circular recess of a plate, and a retaining element (e.g., a shield) can be secured over the wave washer after it has been placed in the circular recess to prevent the wave washer from escaping the recess when a tension load is applied to the plates.

Each assembly enjoys spring-like performance with respect to axial compressive loads, as well as long cycle life to mimic the axial biomechanical performance of the normal human intervertebral disc. The wave washer expands radially and/or circumferentially under a compressive load, only to spring back into its undeflected shape when it is unloaded. As the wave washer compresses and decompresses, the walls of the circular recess of the second plate embodiment maintain the end of the wave washer within a prescribed boundary on the inwardly facing surface of the plate. Certain assemblies withstand tension loads on the outwardly facing surfaces, because (in embodiments having a generally conical or generally semispherical extent) the shield retains the wide end in the circular recess and because (in embodiments using the ball-shaped protuberance) the rivet in the axial bore prevents the ball-shaped protuberance from deflecting, thus preventing it from exiting the curvate socket and because (in embodiments in which the narrow end of a wave washer is secured by a rivet or a rotatable spoked post), the flanged portion of the rivet (or the spokes of the post) prevents the wave washer from escaping the circular recess. Accordingly, in such embodiments, once the plates are secured to the vertebral bones, the assembly will not come apart when a normally experienced tension load is applied to the spine, similar to the tension-bearing integrity of a healthy natural intervertebral disc.

Assemblies having the ball-and-socket joint also provide a centroid of motion centrally located within the intervertebral space, because the plates are made rotatable and angulatable relative to one another by the ball-shaped protuberance being rotatably and angulatably coupled in the curvate socket. The centroid of motion remains in the ball-shaped protuberance, and thus remains centrally located between the vertebral bodies, similar to the centroid of motion in a healthy natural intervertebral disc.

BRIEF DESCRIPTION OF THE DRAWINGS

FIGS. 1.1 through 1.7 show various embodiments of plates of the invention for use in an artificial disc of the invention.

FIGS. 1.1 and 1.2 show a bottom plan view and a side cutaway view, respectively, of a plate having a flat surface on its inwardly facing surface.

FIGS. 1.3 and 1.4 show a bottom plan view and a side cutaway view, respectively, of a plate having a circular recess on its inwardly facing surface.

FIGS. 1.5 and 1.6 show a bottom plan view and a side cutaway view, respectively, of a plate having a ball-shaped protuberance on its inwardly facing surface.

FIG. 1.7 shows a top plan view of any of the plates of FIGS. 1.1 through 1.6 (all appear the same from this view).

FIGS. 2.1 through 2.6 show top views of various embodiments of wave washers of the invention for use in an artificial disc of the invention, to illustrate a variety of circumferential extent configurations and central bore configurations contemplated by the invention.

FIG. 2.1 shows a wave washer having a continuous circumferential extent.

Figure 7:
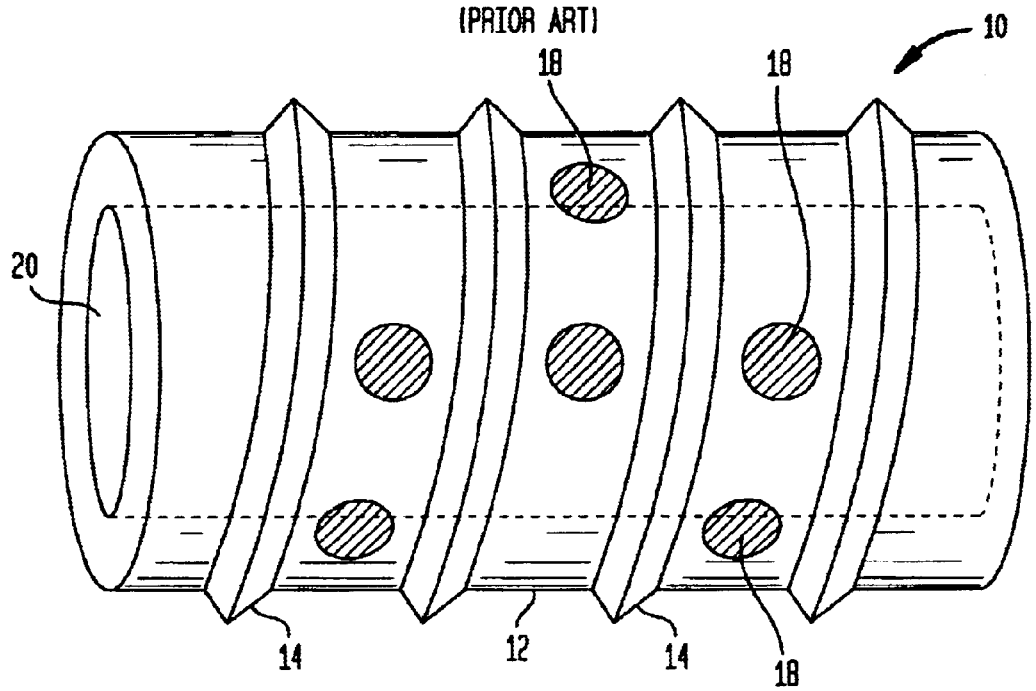

0043 FIG. 2.2 shows a wave washer having a circumferential extent with radially extending slots.

FIG. 2.3 shows a wave washer having a circumferential extent with radially extending and spiraling slots.

FIG. 2.4 shows a wave washer having a continuous circumferential extent and a curvate socket.

FIG. 2.5 shows a wave washer having a circumferential extent with radially extending slots and a curvate socket.

FIG. 2.6 shows a wave washer having a circumferential extent with radially extending and spiraling slots and a curvate socket.

FIGS. 3.1 through 3.14 show side cross-section views and side views of various embodiments of wave washers of the invention for use in an artificial disc of the invention, to illustrate additional varieties of circumferential extent configurations and central bore configurations of the invention.

FIGS. 3.1 and 3.8 show wave washers having a generally planar circumferential extent.

FIGS. 3.2 and 3.9 show wave washers having a generally conical and radially straight circumferential extent.

FIGS. 3.3 and 3.10 show wave washers having a generally semispherical and radially bowed circumferential extent.

FIGS. 3.4 and 3.11 show wave washers having a generally conical and radially straight circumferential extent that has a lower downwardly extending portion and an upper upwardly extending portion.

FIGS. 3.5 and 3.12 show wave washers having a generally semispherical and radially bowed circumferential extent that has a lower downwardly extending portion and an upper upwardly extending portion.

FIGS. 3.6 and 3.13 show wave washers having a generally conical and radially straight circumferential extent and a curvate socket.

FIGS. 3.7 and 3.14 show wave washers having a generally semispherical and radially bowed circumferential extent and a curvate socket.

FIGS. 4.1 through 4.15 show side cross-section views and top views of circumferential extents of various embodiments of wave washers, to illustrate additional varieties of circumferential extent configurations of the invention.

FIG. 4.1 shows a generally straight circumferential extent that is radially wavy.

FIG. 4.2 shows a generally straight circumferential extent that is radially thinning.

FIG. 4.3 shows a generally straight circumferential extent that is radially thickening.

FIG. 4.4 shows a generally straight circumferential extent that is concentrically grooved, with grooves that are similarly dimensioned to one another regardless of their relative radial distance from the central hub.

FIG. 4.5 shows a generally straight circumferential extent that is concentrically grooved, with grooves that become smaller with a greater radial distance of the groove from the central hub.

FIG. 4.6 shows a generally straight circumferential extent that is concentrically grooved, with grooves that become larger with a greater radial distance of the groove from the central hub.

FIG. 4.7 shows a generally bowed circumferential extent that is radially wavy.

FIG. 4.8 shows a generally bowed circumferential extent that is radially thinning.

FIG. 4.9 shows a generally bowed circumferential extent that is radially thickening.

FIG. 4.10 shows a generally bowed circumferential extent that is concentrically grooved, with grooves that are similarly dimensioned to one another regardless of their relative radial distance from the central hub.

FIG. 4.11 shows a generally bowed circumferential extent that is concentrically grooved, with grooves that become smaller with a greater radial distance of the groove from the central hub.

FIG. 4.12 shows a generally bowed circumferential extent that is concentrically grooved, with grooves that become larger with a greater radial distance of the groove from the central hub.

FIG. 4.13 shows a wave washer having a circumferential extent with concentric grooves having a concentrically varying width.

FIGS. 4.14 and 4.15 show a wave washer having a circumferential extent with at least one wave that varies in width and depth along the length of the wave.

FIGS. 5.1 through 5.6 show side views of various assembled artificial disc embodiments of the invention, with plates and shields of the invention in side cutaway view, but wave washers of the invention in side view.

FIG. 5.1 shows a wave washer having a generally planar circumferential extent, disposed between circular recesses of opposing plates.

FIG. 5.2 shows a wave washer having a generally planar circumferential extent, disposed between circular recesses of opposing plates and maintained within the circular recesses by rotatable spoked posts.

FIG. 5.3 shows a wave washer having a generally semi-spherical circumferential extent, disposed between circular recesses of opposing plates.

FIG. 5.4 shows a wave washer having a generally semi-spherical circumferential extent, rotatably secured by a flanged rivet to a flat surface of an upper plate and its wide end seated within a circular recess of a lower plate.

FIG. 5.5 shows a wave washer having a generally semi-spherical circumferential extent and a curvate socket, with its curvate socket coupled to a ball-shaped protuberance of an upper plate and its wide end seated within a circular recess of a lower plate.

FIG. 5.6 shows a wave washer having two wide ends, with its top wide end seated within a circular recess of an upper plate, and its bottom wide end seated within a circular recess of a lower plate.

FIGS. 6.1 through 6.5 show perspective views of additional wave washers of the invention, to illustrate additional varieties of circumferential extent configurations of the invention.

FIG. 6.1 shows a wave washer having a ring-shaped circumferential extent and a radial slot extending fully through the circumferential extent.

FIG. 6.2 shows a wave washer having a spiral-shaped circumferential extent.

FIG. 6.3 shows a plurality of concentrically disposed wave washers, each having a continuous circumferential extent.

FIG. 6.4 shows a wave washer having a spiral-shaped circumferential extent that has peaks and valleys of radially diminishing amplitude.

FIG. 6.5 shows a plurality of concentrically disposed wave washers, each having a continuous circumferential extent, disposed such that wave washers having peaks and valley of greater amplitude are radially close to the center of the plurality.

FIG. 7 shows a side perspective view of a prior art interbody fusion device.

Figure 8:
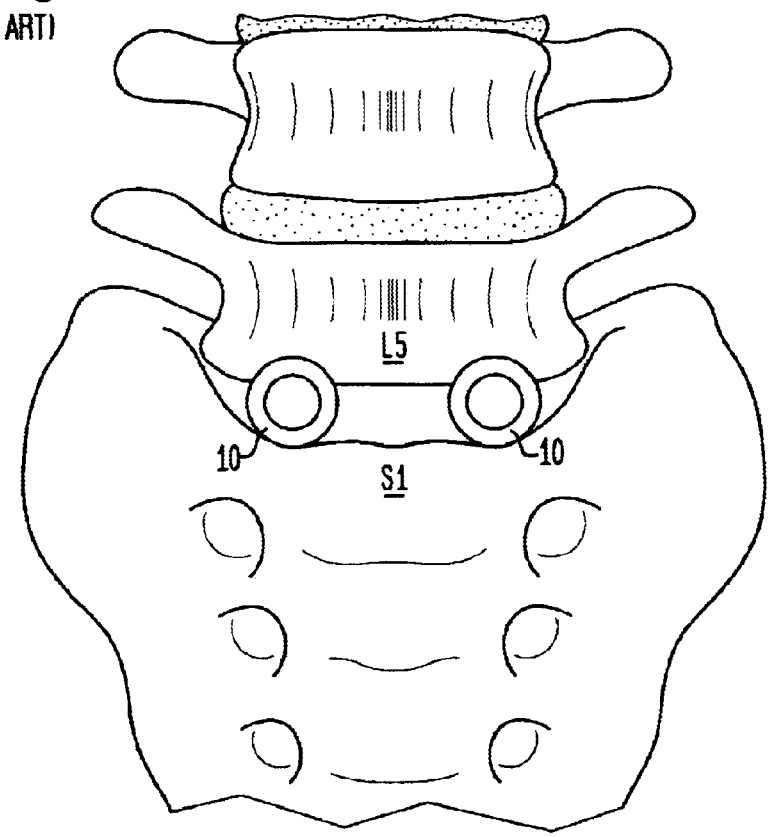

FIG. 8 shows a front view of the anterior portion of the lumbo-sacral region of a human spine, into which a pair of interbody fusion devices of FIG. 7 have been implanted.

DETAILED DESCRIPTION OF THE PREFERRED EMBODIMENTS

While the invention will be described more fully hereinafter with reference to the accompanying drawings, in which particular embodiments and methods of implantation are shown, it is to be understood at the outset that persons skilled in the art may modify the invention herein described while achieving the functions and results of the invention. Accordingly, the descriptions that follow are to be understood as illustrative and exemplary of specific structures, aspects and features within the broad scope of the invention and not as limiting of such broad scope. Like numbers refer to similar features of like elements throughout.

Referring now to FIGS. 1.1 through 1.7, various embodiments of plates of the invention for use in an artificial disc of the invention are shown in bottom plan views (FIGS. 1.1, 1.3, and 1.5), side cutaway views (where cross-sectional areas and surfaces viewable behind them are shown) (FIGS. 1.2, 1.4, and 1.6), and a top plan view (FIG. 1.7). More specifically, FIGS. 1.1 and 1.2 show a bottom plan view and a side cutaway view, respectively, of a first embodiment 100a of a plate. FIGS. 1.3 and 1.4 show a bottom plan view and a side cutaway view, respectively, of a second embodiment 100b of a plate. FIGS. 1.5 and 1.6 show a bottom plan view and a side cutaway view, respectively, of a third embodiment 100c of a plate. FIG. 1.7 shows a top plan view of any of the plates 100a–c (all appear the same from this view). As will be described in greater detail below, depending on the type of wave washer used in a particular embodiment of an artificial disc of the invention, two plates selected (for the manner in which they cooperate with the type of wave washer used in the embodiment) from these three embodiments will be used as opposing plates of the embodiment. Some embodiments of the artificial disc use two plates of the same plate embodiment.

Each plate 100a–c has an exterior surface 108a–c. Because the artificial disc of the invention is to be positioned between the facing surfaces of adjacent vertebral bodies, the two plates used in the artificial disc are disposed such that the exterior surfaces face away from one another (as best seen in FIGS. 5.1 through 5.6, discussed below). The two plates are to mate with the vertebral bodies so as to not rotate relative thereto, but rather to permit the spinal segments to axially compress and bend relative to one another in manners that mimic the natural motion of the spinal segment. This motion is permitted by the performance of a wave washer (described below) disposed between the secured plates. The mating of the plates to the vertebral bodies and the application of the wave washer to the plates are described below.

More particularly, each plate 100a–c is a flat plate (preferably made of a metal such as, for example, titanium) having an overall shape that conforms to the overall shape of the respective endplate of the vertebral body with which it is to mate. Further, each plate 100a–c comprises a vertebral body contact element (e.g., a convex mesh 106a–c) (preferably oval in shape) that is attached to the exterior surface 108a–c of the plate 100a–c to provide a vertebral body contact surface. The mesh 106a–c is secured at its perimeter, by laser welds, to the exterior surface 108a–c of the plate 100a–c. The mesh is domed in its initial undeflected conformation, but deflects as necessary during insertion of the artificial disc between vertebral bodies, and, once the artificial disc is seated between the vertebral bodies, deforms as necessary under anatomical loads to reshape itself to the concave surface of the vertebral endplate. This affords the plate having the mesh substantially superior gripping and holding strength upon initial implantation as compared with other artificial disc products. The mesh further provides an osteoconductive surface through which the bone may ultimately grow. The mesh is preferably comprised of titanium, but can also be formed from other metals and/or non-metals without departing from the scope of the invention.

Each plate 100a–c further comprises at least a lateral ring 110a–c that is osteoconductive, which may be, for example, a sprayed deposition layer, or an adhesive applied beaded metal layer, or another suitable porous coating. This porous ring permits the long-term ingrowth of vertebral bone into the plate, thus permanently securing the prosthesis within the intervertebral space. It shall be understood that this porous layer 110a–c may extend beneath the domed mesh 106a–c as well, but is more importantly applied to the lateral rim of the exterior surface 108a–c of the plate 100a–c that seats directly against the vertebral body.

It should be understood that the convex mesh attachment devices and methods described herein can be used not only with the artificial discs and artificial disc plates described or referred to herein, but also with other artificial discs and artificial disc plates, including, but not limited to, those currently known in the art. Therefore, the description of the mesh attachment devices and methods being used with the artificial discs and artificial disc plates described or referred to herein should not be construed as limiting the application and/or usefulness of the mesh attachment device.

With regard to the disposition of a wave washer between two plates, each of the plates 100a–c comprises features for applying the wave washer thereto, and the various application methods are described below. More specifically, the first plate embodiment 100a includes an inwardly facing surface 104a that includes a flat surface 102a that accepts a fastener (e.g., a screw, plug, dowel or rivet; a rivet 114a is used herein as an example) (shown in FIG. 5.4) for rotatably securing a narrow end of a wave washer thereto.

The second plate embodiment 100b includes an inwardly facing surface 104b that includes a circular recess 102b for rotationally housing an end of a wave washer and allowing the end to expand in unrestricted fashion when the wave washer is compressed, and the inwardly facing surface 104b also accepts fasteners (e.g., screw, plugs, dowels, or rivets; rivets 116b are used herein as examples) (shown in FIGS. 5.4 through 5.6) for securing a retaining element (e.g., a shield 118b) (the purpose and application of the shield are described below and shown on FIGS. 5.4 through 5.6).

The third plate embodiment 100c includes an inwardly facing surface 104c that includes an inwardly directed semispherical (e.g., ball-shaped) protuberance 102c. The ball-shaped protuberance 102c includes a series of slots 120c that render the ball-shaped protuberance 102c radially compressible and expandable in correspondence with a radial pressure (or a radial component of a pressure applied thereto). The ball-shaped protuberance 102c further includes an axial bore 122c that accepts a deflection preventing element (e.g., a screw, plug, dowel, or rivet; a rivet 124c is used herein as an example) (shown in FIG. 5.5). (If a screw is used, the axial bore can be threaded to accept it.) Prior to the insertion of the rivet 124c, the ball-shaped protuberance 102c can deflect radially inward because the slots 120c will narrow under a radial pressure. The insertion of the rivet 124c eliminates the capacity for this deflection. Therefore, the ball-shaped protuberance 102c, before receiving the rivet 124c, can be compressed to seat in a curvate socket of a wave washer and, once the ball-shaped protuberance 102c has been seated in the curvate socket, the rivet 124c can be inserted into the axial bore 122c to ensure that the ball-shaped protuberance 102c remains held in the curvate socket. A hole can be provided in the opposing plate so that the interior of the device may be readily accessed if a need should arise.

The curvate socket has a substantially constant radius of curvature that is also substantially equivalent to the radius of the ball-shaped protuberance with which it mates, so that when the ball-shaped protuberance is secured therein, the ball-shaped protuberance can rotate and angulate freely relative to the curvate socket through a range of angles, thus permitting the opposing plates to rotate and angulate freely relative to one another through a corresponding range of angles equivalent to the fraction of normal human spine rotation and angulation (to mimic normal disc rotation and angulation). It should be understood that the specific dimensions of the ball-shaped protuberance, the mechanism for radial compressibility of the ball-shaped protuberance, and the mechanism for preventing radial compression of the ball-shaped protuberance are not limited to those shown, but rather can be varied and changed without departing from the scope of the invention.

Referring now to FIG. 6.1, an embodiment of a wave washer force restoring element of the invention is provided in a perspective view. The wave washer 610 comprises an undulating ring-shaped circumferential extent 615 (preferably formed from a titanium alloy or stainless steel) having a radial slot 612 that extends fully though the circumferential extent. The circumferential extent 615, while maintaining a constant radius, has undulations (a sinusoidal-type rising and falling of the extent) that create periodic peaks 613 and valleys 611.

It shall be understood that the wave washer 610 can also be provided without a radial break or slot 612, and would thus be continuous. The restoring force of a wave washer (whether continuous or slotted) is proportional to the elastic properties of the material, and these are opposed as the compressive load is applied down onto the peaks 613 and up against the valleys 611. In the case of a continuous wave washer, the loads are translated into hoop stresses that apply stresses directed toward radially expanding the washer. In the case of the radially slotted washer 610, the radial slot 612 permits the compressive load that is applied to the washer (again, down onto the peaks 613 and up against the valleys 611) to cause the washer to radially expand without the build-up of hoop stresses. If the slotted wave washer 610 is radially constrained against such an expansion, the slot 612 is able to close. The wave washer is therefore able to deflect downwardly without radially expanding. Stated equivalently, a difference between the radially slotted wave washer 610 of FIG. 6.1, and a continuous wave washer, is that the continuous wave washer responds to a compressive load by deflecting radially (with a very high stress to deflection ratio), whereas the radially slotted wave washer 610, when radially constrained, deflects circumferentially, closing the slot 612 (which is characteristic of a much lower stress to deflection ratio).

With reference now to FIG. 6.2, another embodiment of a wave washer force restoring element of the invention is provided in perspective view. The wave washer 620 comprises a circumferential extent 625 formed from a spirally wound band of material (as above, a suitable titanium alloy or stainless steel is preferable). As with the ring-shaped wave washer 610 introduced above, the spirally wound wave washer 620 includes a series of alternating and undulating peaks 623 and valleys 621 that extend continuously around the spiral. The spiral wave washer 620 in FIG. 6.2 shows the series of peaks 623 and valleys 621 being radially aligned. Alternatively, it shall be understood that the peaks and valleys may be non-aligned.

With reference to FIG. 6.3, yet another embodiment of a wave washer force restoring element of the invention is provided in perspective view. A plurality of wave washers 630a–c each comprises a circumferential extent 635a–c that is ring-shaped, similar to the wave washer 610 introduced above, but continuous (i.e., it has no radial slot). The wave washers 630a–c are disposed relative to one another so that they are concentric, with the wave washer 630a having the smallest radius being surrounded by the wave washer 630b having the next largest radius, which is in turn surrounded by a wave washer 630c having an even larger radius. The plurality of wave washers 630a–c therefore provides a functionality similar to the spirally wound wave washer 620 introduced above. It should be understood that more or fewer concentric wave washers can be similarly disposed without departing from the scope of the invention. Further, although the peaks 633a–c and valleys 631a–c of the wave washers 630a–c are radially aligned, it shall be understood that alternatively, the peaks and valleys may be radially non-aligned in some embodiments.

With reference now to FIG. 6.4, still another embodiment of a wave washer force restoring element of the invention is provided in perspective view. The wave washer 640 comprises a circumferential extent 645 that is spirally would, similar to the wave washer 620 introduced above, but in which the amplitudes of the peaks 643 and valleys 641 are radially diminishing. This conformation permits a non-linear load-deflection profile that more closely mimics the load-deflection performance of a natural disc. The spiral wave washer 640 in FIG. 6.4 shows the series of peaks 643 and valleys 641 being radially non-aligned. Alternatively, it shall be understood that the peaks and valleys may be radially aligned.

With reference to FIG. 6.5, yet another embodiment of a wave washer force restoring element of the invention is provided in perspective view. A plurality of wave washers 650a–c, formed and disposed similarly to the plurality of wave washers 650a–c introduced above in that each comprises a continuous circumferential extent 655a–c that is ring-shaped, and in that they are disposed relative to one another so that they are concentric, with the wave washer 650a having the smallest radius being surrounded by the wave washer 650b having the next largest radius, which is in turn surrounded by a wave washer 650c having an even larger radius. However, in this embodiment, the inner wave washer 650a has peaks 653a and valleys 651a with amplitudes smaller than the amplitudes of the peaks 653b and valleys 651b of the middle wave washer 650b, which in turn have amplitudes smaller than the amplitudes of the peaks 653c and valleys 651c of the outer wave washer 650c. That is, the amplitudes of the peaks and valleys of the group of wave washers 650a–c decrease with the greater radial distance of the washer from the inner washer. The plurality of wave washers 650a–c therefore provides a functionality similar to the spirally wound wave washer 640 introduced above. It should be understood that more or fewer concentric wave washers can be similarly disposed without departing from the scope of the invention. Further, although the peaks 653a–c and valleys 651a–c of the wave washers 650a–c are radially aligned, it shall be understood that alternatively, the peaks and valleys may be radially non-aligned in some embodiments.

With regard to additional wave washer embodiments, changing the configuration of the circumferential extent in other ways modifies the magnitude of the compressive load support and restoring force provided by the wave washer. For clarity and conciseness, the other circumferential extent configurations discussed hereinbelow are illustrated with regard to wave washers having circumferential extents that are ring-shaped (as opposed to spiral-shaped) and thicker compared to the wave washer embodiments summarized above (as those summarized embodiments are illustrated), however it should be understood that the additional circumferential extent variations discussed herein can be applied individually or in various combinations to the spiral-shaped, concentric, and/or radially decreasing undulation amplitude configurations, without departing from the scope of the invention.

Referring now to FIGS. 2.1 through 2.6, top views of various additional embodiments of wave washers of the invention for use in an artificial disc of the invention are shown to illustrate a variety of additional wave washer configurations and central bore configurations that are merely a subset of the wave washer configurations and central bore configurations contemplated by the invention. More specifically, each wave washer (e.g., 200a–u) has a circumferential extent (e.g., 202a–u) surrounding a central bore (e.g., 206a–u). The circumferential extent is concentrically wavy, such that the extent undulates along a concentric path around the central bore to form radially extending valleys (e.g., 208a–g) and peaks (e.g., 210a–g) (best shown by examples on FIGS. 3.8 through 3.14, discussed below) while preferably maintaining a constant radius. In some embodiments (e.g., 200a–g), the circumferential extent (e.g., 202a–g) is continuous (i.e., has no slots). In other embodiments (e.g., 200h–n), the circumferential extent (e.g., 202h–n) has radially extending slots (e.g., 212h–n). In still other embodiments (e.g., 200o–u), the circumferential extent (e.g., 202o–u) has radially extending and spiraling slots (e.g., 212o–u). The frequency, amplitude, and configuration of the waves and/or the number and configuration of the slots can be varied to accommodate any desired application, inasmuch as varying the dimensions will affect the behavior of the wave washer in expansion and retraction.

The restoring force of a wave washer is proportional to the elastic properties of the material. As a compressive load is applied to the wave washer, the forces are directed down onto the peaks and up against the valleys. A significant fraction of these forces are immediately translated into hoop stresses that apply stresses directly toward radially expanding the wave washer. This hoop stress is also counterbalanced by the material strength of the wave washer. The strain of the material causes a deflection in the height of the washer and a slight radial expansion. The slots in the slotted embodiments permit the compressive load that is applied to the wave washer down onto the peaks and up against the valleys to cause the wave washer to deflect such that the slots close. Thus, a difference between a slotted washer and a continuous washer is that the continuous washer responds to a compressive load by primarily deflecting radially (with a very high stress to deflection ratio), whereas the slotted washer deflects primarily circumferentially, closing the slots (which is characteristic of a much lower stress to deflection ratio). Stated equivalently, a wave washer responds to a compressive load by deflecting compressively and either radially or circumferentially. With at least one slot formed in the washer, it expands and retracts far more elastically than a continuous washer. It should be understood that wave washers other than those shown are contemplated by the invention, including but not limited to wave washers having a circumferential extent that does not have a uniformly wide radius.

With regard to the central bore configurations 206a–u shown on FIGS. 2.1 through 2.6, these are discussed in greater detail below with reference to FIGS. 5.1 through 5.6 regarding methods of applying the wave washers to the plates discussed above. However, for properly understanding the discussions of FIGS. 3.1 through 3.14 and 4.1 through 4.15 below, it is important to summarize here that some wave washer embodiments (e.g., 200a–e,h–l,o–s) have a simple bore (e.g., 206a–e,h–l,o–s), and other wave washer embodiments (e.g., 200f–g,m–n,t–u) have a bore that forms a curvate socket (e.g., 206f–g,m–n,t–u) of a type described above with regard to being mateable with the semispherical protuberance described above.

Referring now also to FIGS. 3.1 through 3.14, side cross-section views (where only the cross-sectional area is shown) and corresponding side views (some with side cross-section views shown in phantom for clarity) of various embodiments of wave washers are shown to illustrate additional varieties of wave washer configurations and central bore configurations that are merely a subset of the wave washer configurations and central bore configurations contemplated by the invention. The side cross-sections are taken along cut lines A1–A1', F1–F1', H–H', M–M', O–O', and T–T' on FIGS. 2.1 through 2.6, as applicable, and the side views are taken along cut lines A2–A2' and F2–F2' on FIGS. 2.1 and 2.4, as applicable.

It should be understood that the use of multiple reference numbers for various elements are used throughout the figures to indicate where a single view illustrates more than one wave washer embodiment, given that some wave washers look similar from certain views but not similar from other views. This has been done to consolidate illustrations for conciseness and clarity. For example, FIGS. 3.1 through 3.5 illustrate wave washer embodiments that from a top view appear as any of FIGS. 2.1 through 2.3. Also, for example, FIGS. 3.6 and 3.7 illustrate wave washer embodiments that from a top view appear as any one of FIGS. 2.4 through 2.6. Stated alternatively, each of FIGS. 3.1 through 3.7 is not a side cross-section view that is associated with only one of the top views of FIGS. 2.1 through 2.6, but rather is associatable with more than one of the top views of FIGS. 2.1 through 2.6. And, for example, FIGS. 3.8 through 3.12 are side views corresponding respectively to the side cross-section views of FIGS. 3.1 through 3.5, but only with regard to certain wave washer embodiments (e.g., 200a–e), as noted by reference numbers, and FIGS. 3.13 and 3.14 are side views corresponding respectively to the side cross-section views of FIGS. 3.6 and 3.7, but only with regard to certain wave washer embodiments (e.g., 200f–g), as noted by reference numbers. It should be understood, however, that certain configurations of wave washer embodiments (e.g., 200h–l,o–s) would have similar side view appearances as FIG. 3.8 through 3.12, and that certain configurations of wave washer embodiments (e.g., 200m–n,t–u) would have similar side view appearances as FIG. 3.13 through 3.14, except for the presentation of straight or spiral slots, as applicable.

More specifically, FIG. 3.1 shows a configuration where the circumferential extent of the wave washer (e.g., 200a, h,o) is generally planar (e.g., the extent extends in a plane and all of the waves undulate perpendicular to that plane). FIGS. 3.2, 3.4, and 3.6 show configurations where the circumferential extent of the wave washer (e.g., 200b,d,f,i, k,m,p,r,t) is generally conical (e.g., the extent extends to define a conical surface concentric with the central bore and the waves undulate perpendicular to that surface at their respective positions on the surface) and radially straight, such that the height of the wave washer is linearly related to the radial width of the circumferential extent. FIGS. 3.3, 3.5, and 3.7 show configurations where the circumferential extent of the wave washer (e.g., 200c,e,g,j,l,n,q,s,u) is generally semispherical (e.g., the extent extends to define a semispherical surface concentric with the central bore and the waves undulate perpendicular to that surface at their respective positions on the surface) and radially bowed, such that the height of the wave washer is not linearly related to the radial width of the circumferential extent (but rather the wave washer may, for example, be parabolic in shape). FIGS. 3.2, 3.3, 3.6 and 3.7 show configurations in which the circumferential extent of the wave washer (e.g., 200b,c,f,g, i,j,m,n,p,q,t,u) extends radially downwardly from the central bore. FIGS. 3.4 and 3.5 show configurations in which the circumferential extent of the wave washer (e.g., 200d,e,k,l, r,s) is doubled, with a lower portion extending radially downwardly from the central bore and an upper portion extending radially upwardly from the central bore.

Further with regard to the central bores shown in top views on FIGS. 2.1 through 2.6, these are shown in side cross-section views in FIGS. 3.1 through 3.7, with some also shown in side cross-section views in phantom in FIGS. 3.13 and 3.14. More specifically, simple bores (e.g., 206a–e,h–l, o–s) are shown in side cross-section views in FIGS. 3.1 through 3.5. Bores that form curvate sockets (e.g., 206f–g, m–n,t–u) are shown in side cross-section views in FIGS. 3.6 and 3.7 and some of those (e.g., 206f–g) are also shown in side cross-section views in phantom in FIGS. 3.13 and 3.14.

Referring now also to FIGS. 4.1 through 4.12, side cross-section views (where only the cross-sectional area is shown) of circumferential extents (e.g., 202aa–ll) of various embodiments of wave washers are shown to illustrate additional varieties of wave washer configurations that are merely a subset of the wave washer configurations contemplated by the invention. The side cross-sections are taken from the inner edge of the circumferential extent (i.e., the edge of the central bore of the wave washer) radially to the outer edge of the circumferential extent. It should be understood that with regard to the remaining structure of the wave washers having the illustrated circumferential extents, the wave washers can share all or some of the features (e.g., bore configurations, double extent configurations, slot configurations, etc.) of the other wave washer embodiments discussed herein, and/or have features that are different and/or configured differently.

More specifically, FIGS. 4.1 through 4.12 show configurations where the circumferential extent of the wave washer is generally conical (FIGS. 4.1 through 4.6) (the waves undulate about a conical surface concentric with the central bore) and radially straight, such that the height of the wave washer is linearly related to the radial width of the circumferential extent, or generally semispherical (FIGS. 4.7 through 4.12) (the waves undulate about a semispherical surface concentric with the central bore) and radially bowed, such that the height of the wave washer is not linearly related to the radial width of the circumferential extent, but additionally have at least one concentric or radial characteristic (in addition to the concentric waviness common to all of the wave washer embodiments) that alters the performance of the wave washer in expansion and/or retraction. For example, the circumferential extents in FIGS. 4.1 and 4.7 are not only concentrically wavy, but are also radially wavy. Also for example, the circumferential extents in FIGS. 4.2 and 4.8 are radially thinning (the portion of the extent near the central bore is thicker than the portion of the extent near the outer edge of the washer). Also for example, the circumferential extents in FIGS. 4.3 and 4.9 are radially thickening (the portion of the extent near the central bore is thinner than the portion of the extent near the outer edge of the washer). Also for example, the circumferential extents in FIGS. 4.4, 4.5, 4.6, 4.10, 4.11 and 4.12 are concentrically grooved, having grooves that are similarly dimensioned to one another regardless of their relative radial distance from the central bore (FIGS. 4.4 and 4.10), or grooves that vary in dimension from one another depending on their relative radial distance from the central bore (FIGS. 4.5, 4.6, 4.11 and 4.12). For example, the width and depth of the grooves in FIG. 4.5 and the grooves in FIG. 4.11 become smaller with the greater radial distance of the groove from the central bore. And, for example, the width and depth of the grooves in FIG. 4.6 and the grooves in FIG. 4.12 become larger with the greater radial distance of the groove from the central bore.

In some embodiments, at least one dimension of a concentric groove (such as, for example, the width and/or depth) can be applied to vary concentrically across the circumferential extent. FIG. 4.13 shows one example of a configuration where two concentric grooves 211v, 212v, each concentrically varying in width, are applied to the circumferential extent 202v of a wave washer 200v.

It should be noted that with regard to the waves of the wave washers of the invention, one or both of the depth and the width of each wave can be (1) decreasing along the length of the wave from the outer edge of the washer toward the central bore, (2) increasing along the length of the wave from the outer edge of the washer toward the central bore, (3) uniform along the length of the wave from the outer edge of the washer toward the central bore, or (4) varied along the length of each wave from the outer edge of the washer toward the central bore, either randomly or according to a pattern. A wave washer embodiment 200w having a circumferential extent 202w, as an example of case (1), is shown in top view in FIG. 4.14 (with dashed lines identifying the tangents of the adjacent peaks that define the wave) and in circumferential extent side cutaway view in FIG. 4.15 (taken along cut lines W–W' in FIG. 4.14), where both the width and depth of a wave 213w vary along the length of the wave. Moreover, it can be the case that each wave is not formed similarly to one or more other waves, but rather one or more waves are formed in any of the above-mentioned fashions, while one or more other waves are formed in another of the above-mentioned fashions or other fashions. It should be clear that any wave pattern can be implemented without departing from the scope of the invention.

It should be understood that the circumferential extents contemplated by the invention include, but are not limited to, those having only one concentric or radial characteristic at a time. The use of more than one concentric or radial characteristic per arm is contemplated, as well as the use of concentric and radial characteristics simultaneously. Further, it is contemplated that some wave washer embodiments will use only a radially straight circumferential extent, some wave washer embodiments will use only a radially bowed circumferential extent, and some wave washer embodiments that will use a circumferential extent that is radially straight in some portions and radially bowed in other portions.

Each of the wave washers is suitable for disposition between two opposing plates of the invention. As noted above, and as discussed in greater detail below, depending on the type of wave washer used in the particular embodiment of the artificial disc of the invention, the two plates are selected (for the manner in which they cooperate with the type of wave washer used in the embodiment) from the three plate embodiments, for use as opposing plates of the embodiment. Some embodiments of the artificial disc use two plates of the same plate embodiment. In each embodiment, the plates are made rotatable and angulatable relative to one another (to mimic the functionality of a healthy natural intervertebral disc) by having a wave washer between the plates, and/or by the manner in which the wave washer is secured to one or both of the plates. Further in each embodiment, the same couplings, and/or through the use of additional coupling elements (e.g., shields, rivets, and/or rotatable spoked posts), enable the artificial disc embodiments to withstand tension loading (to mimic the functionality of a healthy natural intervertebral disc). Further in embodiments having a wave washer, the wave washer enables the artificial disc embodiments to axially compress and axially restore (to mimic the functionality of a healthy natural intervertebral disc).

Referring now also to FIGS. 5.1 through 5.6, these figures show side views of various assembled artificial disc embodiments contemplated by the invention. The side views show the plates in side cutaway view, but the wave washers in side view (with primary cross-sections and couplings in phantom in some figures for clarity). It should be understood that the illustrated embodiments do not encompass all embodiments contemplated by the invention, but rather were selected for illustration purposes to show how the features of the various illustrated plate embodiments cooperate with corresponding features of the various illustrated wave washer embodiments, when the wave washers are disposed between opposing plates of the invention. While only certain assembled artificial disc embodiments are shown, it should be understood that wave washers not shown but having like plate coupling features can be secured to cooperating plates in the manner illustrated, in various permutations and combinations, and the same have been withheld from illustration for purposes of conciseness and clarity only to avoid duplicative illustration that would visually reiterate that which can be understood from the descriptions and illustrations herein.

For example, any of the wave washers can be disposed between circular recesses on inwardly facing surfaces of opposing plates (e.g., the circular recess 102b on the inwardly facing surface 104b of plate 100b). FIGS. 5.1 and 5.2 illustrate this disposition with wave washers (e.g., 200a) having a circumferential extent that is generally planar (see, e.g., FIGS. 3.1 and 3.8). (It should be understood that any of the wave washer embodiments of FIGS. 6.1 through 6.5, and similar embodiments, can be substituted for the wave washer 200a in FIGS. 5.1 and 5.2 and be similarly disposed as shown and/or coupled as shown with plates having circular recesses on inwardly facing surfaces to form additional artificial disc embodiments not specifically illustrated.) FIG. 5.3 illustrates this disposition with a wave washer (e.g., 200c) having a circumferential extent that is generally semispherical (see, e.g., FIGS. 3.3 and 3.10), although the same disposition can be made with a wave washer (e.g., 200b) having a circumferential extent that is generally conical (see, e.g., FIGS. 3.2 and 3.9). FIG. 5.6 illustrates this disposition with a wave washer (e.g., 200e) having a doubled circumferential extent that forms two generally semispherical portions and opposing wide ends (see, e.g., FIGS. 3.5 and 3.12), although the same disposition can be made with a wave washer (e.g., 200d) having a doubled circumferential extent that forms two generally conical portions and opposing wide ends (see, e.g., FIGS. 3.4 and 3.11). In each of these assemblies, each end of the wave washer fits within a respective circular recess 102b with room to expand when the wave washer is under compression. Because the diameter of the circular recess is greater than the diameter of the wave washer, unrestrained rotation of the wave washer relative to the plate having the circular recess is enabled, and compressive loading of the artificial disc (and therefore the wave washer) results in an unrestrained deflection of the wave washer, both as necessary for proper anatomical response. Further in each of these and similarly constructed assemblies, the plates are rotatable relative to one another because the ends of the wave washer can rotate with respect to the plate having the circular recess in which the end seats as indicated above. Further, the plates are angulatable relative to one another because the waves of the wave washer can individually compress and restore, enabling one side of the circumferential extent to compress and restore as the plates angulate relative to one another, while other portions of the circumferential extent do not.

Additional components can be applied in these assemblies in order to prevent removal of the wave washer from the circular recess(es) when the artificial disc is loaded in tension. As an initial matter, if rotation of a wave washer with respect to one of the plates is not desirable, a simple fastener (e.g., a screw, plug, dowel or rivet) can be used to secure the circumferential extent of the wave washer to a circular recess or a flat surface of an inwardly facing surface of a plate so that the wave washer can still compress and decompress, but cannot rotate with respect to the plate to which it is attached. Alternatively, FIG. 5.2 illustrates an example of how a wave washer (e.g., 200a) having a circumferential extent that is generally planar can be rotationally maintained between circular recesses. Opposing rotatable posts 114b (each having at least one spoke 113b extending laterally from an end of the post 114b) can be rotatably installed, one to each of the plates, so that the spokes align with the peaks and valleys of the wave washer, and the post is rotatable with respect to the plate. More specifically, an upper spoked post is applied with its post portion through the bore and its spokes bearing under the peaks to capture the peaks between the spokes and the upper plate, and a lower spoked post is applied with its post portion through the bore and its spokes bearing over the valleys to capture the peaks between the spokes and the lower plate. In this manner, the wave washer is held against both of the plates so that the assembly maintains its integrity under a tension load while still permitting the washer to compress. It should be understood that one or both of the spoked posts can alternatively or additionally be formed from multiple parts, in order to facilitate easy construction of the assembly. It should also be understood that other flanged fasteners can be used instead of a spoked post.

With regard to preventing the removal of the wide ends of wave washers (e.g., 200b–g) having generally conical or generally semispherical circumferential extents from the circular recess(es) when the artificial disc is loaded in tension, FIGS. 5.4 through 5.6 illustrate a retaining element (e.g., a shield 118b) that can be placed over the wave washer and secured by fasteners (e.g., screws, plugs, dowels, or rivets; rivets 116b are used herein as examples). The shield 118b can have a central hole 120b through which the curvate socket (discussed below with regard to FIG. 5.5) and the ball-shaped protuberance (discussed below with regard to FIG. 5.5) can pass to accommodate efficient assembly of the artificial disc. The shield 118b can alternatively or additionally be formed from multiple shield parts, which would be useful, for example, in embodiments where no part of the wave washer can pass through the central hole 120b (see, e.g., the embodiment of FIG. 5.6, discussed below).

A wave washer that has a simple central bore (see, e.g., FIGS. 2.1 through 2.3) and a circumferential extent that is generally conical (see, e.g., FIGS. 3.2 and 3.9) or generally semispherical (see, e.g., FIGS. 3.3 and 3.10) can be disposed with its wide end against a circular recess on an inwardly facing surface of a plate (e.g., the circular recess 102b on the inwardly facing surface 104b of plate 100b) as described above, and its narrow end rotatably secured to a flat surface on an inwardly facing surface on an opposing plate (e.g., the flat surface 102a on the inwardly facing surface 104a of plate 100a). As shown in FIG. 5.4, the narrow end of the wave washer (e.g., 200b–c) can be rotatably secured to the flat surface 104a with a flanged fastener (e.g., a flanged screw, plug, dowel or rivet; a flanged rivet 114a is used herein as an example) passing through the central bore of the wave washer and secured to the flat surface 104a of the plate 100a. The flanged rivet 114a has a flanged portion at the end of a post portion. The post portion has a diameter smaller than the diameter of the bore, and a length that is longer than the thickness of the wave washer extent surrounding the central bore, and the flanged portion has a diameter greater than the diameter of the bore. Therefore, upon application of the rivet 114a, the wave washer is secured to the plate 100a so that it can still rotate with respect to the plate 100a. (A threaded bore in the plate can also be used in conjunction with a similarly flanged screw to achieve the same functionality.) As also discussed above with regard to the securing of the wide end of the wave washer, the plates are secondarily rotatable relative to one another because the wide end of the wave washer can rotate with respect to the plate having the circular recess in which the wide end seats. Further, the plates are angulatable relative to one another because the waves of the wave washer can individually compress and restore, enabling one side of the circumferential extent to compress and restore as the plates angulate relative to one another, while other portions of the circumferential extent do not.

A wave washer that has a central bore that forms a curvate socket (see, e.g., FIGS. 2.4 through 2.6) and a circumferential extent that is generally conical (see, e.g., FIGS. 3.6 and 3.13) or generally semispherical (see, e.g., FIGS. 3.7 and 3.14) can be disposed with its wide end against a circular recess on an inwardly facing surface of a plate (e.g., the circular recess 102b on the inwardly facing surface 104b of plate 100b) as described above, and its narrow end rotatably and angulatably coupled with a semispherical protuberance on an inwardly facing surface on an opposing plate (e.g., the ball-shaped protuberance 102c on the inwardly facing surface 104c of plate 100c). As shown in FIG. 5.5, the central bore of such a wave washer (e.g., 200f–g) preferably forms a curvate socket (e.g., 206f–g,m–n,t–u) within which the ball-shaped protuberance 102c is securable for free rotation and angulation through a range of angles. The structure of the curvate socket and the coupling of the ball-shaped protuberance with the curvate socket are as described above. As noted above, a deflection preventing element (e.g., a screw, plug, dowel, or rivet 124c) applied to the axial bore 122c after the ball-shaped protuberance 102c has been inserted into the curvate socket prevents the deflection of the ball-shaped protuberance 102c so that it does not escape the curvate socket. The plates are rotatable relative to one another primarily because the ball-shaped protuberance rotates freely within the curvate socket, and secondarily because the wide end of the wave washer can rotate with respect to the plate having the circular recess in which the wide end seats (discussed below). Also, the plates are angulatable relative to one another primarily because the ball-shaped protuberance angulates freely within the curvate socket, and secondarily because the waves of the wave washer can individually compress and restore, enabling one side of the circumferential extents to compress and restore as the plates angulate relative to one another, while other portions of the circumferential extent do not.

In embodiments having a ball-and-socket joint as described above, because the ball-shaped protuberance is held within the curvate socket by a rivet in the axial bore preventing radial compression of the ball-shaped protuberance, the artificial disc can withstand tension loading of the plates, as necessary for proper anatomical response. More particularly, when a tension load is applied to the plates, the ball-shaped protuberance in the curvate socket seeks to radially compress to fit through the opening of the curvate socket. However, the rivet in the axial bore of the ball-shaped protuberance prevents the radial compression, thereby preventing the ball-shaped protuberance from exiting the curvate socket. Further, in embodiments that have a wave washer with a generally conical or generally semispherical circumferential extent, as the wide end of the wave washer seeks to escape the circular recess of the plate, the rivets holding the shield in place over the wave washer prevent the shield from separating from the plate when the wave washer presses against the inner surface of the shield. Further, in embodiments where the narrow end of the wave washer is rotatably secured against a plate by a rivet, the flanged portion of the rivet prevents the separation of the narrow end of the wave washer. Therefore, the assembly does not come apart under normally experienced tension loads. This ensures that no individual parts of the assembly will pop out or slip out from between the vertebral bodies when the patient stretches or hangs while exercising or performing other activities. Thus, in combination with the securing of the plates to the adjacent vertebral bones via the mesh domes, the disc assembly has an integrity similar to the tension-bearing integrity of a healthy natural intervertebral disc.

Further, because the plates in some embodiments are made angulatable relative to one another by the ball-shaped protuberance being rotatably and angulatably coupled in a curvate socket, the disc assembly provides a centroid of motion within the ball-shaped protuberance. Accordingly, in those embodiments, the centroid of motion of the disc assembly remains centrally located between the vertebral bodies, similar to the centroid of motion in a healthy natural intervertebral disc.

While there has been described and illustrated specific embodiments of an artificial disc, it will be apparent to those skilled in the art that variations and modifications are possible without deviating from the broad spirit and principle of the invention. The invention, therefore, shall not be limited to the specific embodiments discussed herein.

What is claimed is:

1. An intervertebral spacer device, comprising:
   first and second plates, said plates being disposed in a spaced apart relationship such that a plate surface of said first plate faces a plate surface of said second plate, said facing surfaces being inner surfaces, and alternative faces of each plate being outer surfaces; and
   at least one restoring force providing element disposed between the inner surfaces of said first and second plates, and disposed such that a compressive load applied to the outer surfaces of said first and second plates is counteracted by said at least one restoring force providing element, said at least one restoring force providing element including at least one wave washer selected from the group consisting of a conical-shaped wave washer, a semispherical-shaped wave washer, and a wave washer having two wide ends separated by a narrower centrally bored portion from which an upwardly extending circumferential extent portion extends to form one of the wide ends and from which a downwardly extending circumferential extent portion extends to form the other of the wide ends.

2. The intervertebral spacer device of claim 1, wherein at least one of said first and second plates comprises a post mounted to its inner surface, the post having a plurality of laterally extending spokes, and the at least one wave washer is secured to the at least one of said first and second plates with a circumferential extent of the at least one wave washer being maintained between the spokes and the at least one of said first and second plates.

3. The intervertebral spacer device of claim 1, wherein at least one of said first and second plates comprises a flanged fastener mounted to its inner surface, the flanged fastener having a post portion and a flanged portion, and wherein the post portion has a diameter smaller than a diameter of a central bore of the at least one wave washer, and a length greater than a thickness of a portion of a circumferential extent, of the at least one wave washer, surrounding the central bore, and wherein the flanged portion has a diameter greater than the diameter of the central bore, and wherein the at least one wave washer is secured to the at least one of said first and second plates with the circumferential extent portion surrounding the central bore being maintained between the flanged portion and the at least one of said first and second plates.

4. The intervertebral spacer device of claim 1, wherein the at least one wave washer has a circumferential extent thickness that is radially varying.

5. The intervertebral spacer device of claim 1, wherein the at least one wave washer has a circumferential extent that is radially wavy.

6. The intervertebral spacer device of claim 1, wherein the at least one wave washer has a circumferential extent that has at least one concentric groove.

7. The intervertebral spacer device of claim 6, wherein the at least one concentric groove has a depth and a width, and wherein at least one of the width and the depth varies along a length of the concentric groove.

8. The intervertebral spacer device of claim 1, wherein the at least one wave washer has a circumferential extent having at least one radially extending wave valley having a depth and a width, and wherein at least one of the depth and the width of the valley radially varies.

9. The intervertebral spacer device of claim 1, wherein the at least one wave washer comprises a central bore and a doubled circumferential extent extending from the central bore, the doubled circumferential extent having the upwardly extending circumferential extent portion and the downwardly extending circumferential extent portion.

10. The intervertebral spacer device of claim 9, wherein at least one of the portions is conical-shaped.

11. The intervertebral spacer device of claim 9, wherein at least one of the portions is semispherical-shaped.

12. An artificial intervertebral disc, comprising:
   first and second plates disposed to provide opposed respective inwardly facing support surfaces of said plates, and to provide respective outwardly facing vertebral body contact surfaces of said plates; and
   at least one wave washer disposed between the inwardly facing support surfaces such that a compressive load applied to the outwardly facing vertebral body contact surfaces is resisted by said at least one wave washer; wherein
      said at least one wave washer includes a central bore forming a curvate socket; and wherein
         at least one of said first and second plates includes on its inwardly facing support surface a semispherical protuberance that is rotatably and angulatably couplable to the curvate socket such that the plates are rotatable and angulatable relative to one another thereby.

13. The artificial intervertebral disc of claim 12, wherein the semispherical protrusion comprises a radially deflectable semispherical portion and the curvate socket has an interior volume and an opening leading to the interior volume, the curvate socket accommodating the semispherical portion for free rotation and angulation therein, the semispherical portion fitting through the opening only when radially deflected, the semispherical portion being adapted to receive a deflection preventing element that when applied to the semispherical portion prevents the semispherical portion from fitting through the opening.

14. The artificial intervertebral disc of claim 13, wherein the semispherical protuberance comprises at least one radial slot such that the semispherical protuberance is radially deflectable upon the application of a radially inwardly directed force.

15. The artificial intervertebral disc of claim 14, wherein the semispherical protuberance further comprises an axial bore into which the deflection preventing element is disposable to prevent the radial deflection of the semispherical protuberance.

16. The artificial intervertebral disc of claim 12, wherein said at least one wave washer is selected from the group consisting of a ring-shaped wave washer, a spiral-shaped wave washer, a conical-shaped wave washer, and a semispherical-shaped wave washer.

17. An artificial intervertebral disc, comprising:
first and second plates disposed to provide opposed respective inwardly facing support surfaces of said plates, and to provide respective outwardly facing vertebral body contact surfaces of said plates; and
at least one wave washer rotatably coupled to the inwardly facing support surface of at least one of said first and second plates by a wave washer securing element such that the plates are made rotatable relative to one another thereby, and such that a compressive load applied to the outwardly facing vertebral body contact surfaces is resisted by said at least one wave washer.

18. The artificial intervertebral disc of claim 17, wherein the wave washer securing element comprises a post having at least one laterally extending spoke, and said at least one wave washer is secured to the at least one of said first and second plates with a circumferential extent of said at least one wave washer being maintained between the at least one laterally extending spoke and the at least one of said first and second plates.

19. The artificial intervertebral disc of claim 17, wherein the wave washer securing element comprises a flanged fastener having a post portion and a flanged portion, and wherein the post portion has a diameter smaller than a diameter of a central bore of said at least one wave washer, and a length greater than a thickness of a portion of a circumferential extent of said at least one wave washer surrounding the central bore, and wherein the flanged portion has a diameter greater than the diameter of the central bore, and wherein said at least one wave washer is secured to the at least one of said first and second plates with the circumferential extent portion surrounding the central bore being maintained between the flanged portion and the at least one of said first and second plates.

20. The artificial intervertebral disc of claim 17, wherein said at least one wave washer is selected from the group consisting of a ring-shaped wave washer, a spiral-shaped wave washer, a conical-shaped wave washer, and a semispherical-shaped wave washer.

* * * * *